United States Patent [19]

Takamizawa et al.

[11] 4,308,212
[45] Dec. 29, 1981

[54] NOVEL FLUORINE-CONTAINING ORGANOSILANE COMPOUNDS

[75] Inventors: Minoru Takamizawa; Yoshio Inoue; Hiroshi Yoshioka, all of Annaka, Japan

[73] Assignee: Shin-Etsu Chemical Co., Ltd., Tokyo, Japan

[21] Appl. No.: 144,927

[22] Filed: Apr. 29, 1980

[30] Foreign Application Priority Data

May 10, 1979 [JP] Japan ............................. 54-57362

[51] Int. Cl.³ ................................................ C09F 7/00
[52] U.S. Cl. ..................................... 260/408; 556/442
[58] Field of Search ......................... 260/408; 556/442

[56] References Cited

U.S. PATENT DOCUMENTS 3,478,076  11/1969  Kim et al. ............................ 260/408
4,007,313  2/1977  Higuchi et al. ....................... 260/408

*Primary Examiner*—John F. Niebling
*Attorney, Agent, or Firm*—Toren, McGeady & Stanger

[57] ABSTRACT

The invention provides a novel class of organosilane compound represented by the general formula $$X\text{---}(CF_2\text{---}CF_2)_n\text{---}CH_2\text{---}CH_2\text{---}Si(OCOR^2)_m(R^1)_{3-m}$$

in which $R^1$ is a monovalent hydrocarbon group having from 1 to 6 carbon atoms, $R^2$ is a monovalent hydrocarbon group having from 7 to 21 carbon atoms, X is a hydrogen atom or a fluorine atom, n is a positive integer not exceeding 4 and m is a positive integer not exceeding 3. The fluoroalkyl-containing acyloxy silanes are useful as an additive ingredient in a synthetic resin composition for shaping articles or a coating composition with a synthetic resin as the vehicle when improved lubricity is desired on the surface of the shaped article or on the coated surface.

5 Claims, No Drawings

NOVEL FLUORINE-CONTAINING ORGANOSILANE COMPOUNDS

BACKGROUND OF THE INVENTION

The present invention relates to a novel fluorine-containing organosilane compound and uses thereof for improving surface properties of various kinds of synthetic resin articles. In particular, the present invention relates to a novel organosilane compound having fluoroalkyl groups and acyloxy groups bonded to the silicon atom, which compound being useful for imparting lubricity or releasability to the surface of shaped articles of synthetic resins.

It is a very conventional practice that a shaped article of a synthetic resin is imparted with improved surface lubricity or releasability to have a decreased coefficient of friction by coating the surface of the article with or by admixing the molding compound for shaping the article with a lubricating agent such as waxes, e.g. paraffin waxes, carnauba wax, polyethylene waxes and the like, metal soaps and oils or fats as well as certain silicone fluids, e.g. dimethylsilicone fluids and methylphenylsilicone fluids.

Among the above mentioned lubricating agents, dimethylsilicone fluids are most widely used owing to the excellent mold releasability and good lubricating performance compatible with almost all kinds of synthetic resins as well as their inertness and high heat stability. Nevertheless, even the dimethylsilicone fluids are not always perfectly satisfactory depending on the kind of the particular synthetic resins and particular manners of use of the articles with somewhat insufficient compatibility with the resin. Therefore, the improving effect of the surface properties of a shaped article of a synthetic resin obtained by admixing a dimethylsilicone fluid is sometimes not lasting.

SUMMARY OF THE INVENTION

It is therefore a primary object of the present invention to provide a novel and improved means for improving the surface properties of a shaped article of a synthetic resin.

Another object of the invention is to provide a novel class of organosilicon compounds capable of imparting durable improving effects of surface properties to a shaped article of a synthetic resin when admixed into the molding compound for shaping the article.

The novel organosilicon compounds provided by the invention are the organosilane compounds having fluoroalkyl groups and acyloxy groups bonded to the silicon atom and represented by the following general formula

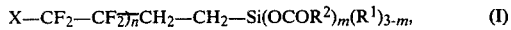   (I)

in which $R^1$ is a monovalent hydrocarbon group having from 1 to 6 carbon atoms, $R^2$ is a monovalent hydrocarbon group having from 7 to 21 carbon atoms, X is a hydrogen atom or a fluorine atom, n is a positive integer not exceeding 4 and m is a positive integer not exceeding 3.

The above defined organosilane compound is admixed with a synthetic resin for shaping articles in an amount from 0.01 to 20 parts by weight per 100 parts by weight of the resin to exhibit excellent improving effects of surface properties with high durability to the articles shaped with the resin composition.

DETAILED DESCRIPTION OF THE PREFERRED EMBODIMENTS

The novel organosilane compounds of the invention represented by the general formula (I) above are readily obtained by the dehydrochlorination reaction between a fluoroalkyl-containing mono-, di- or trichlorosilane represented by the general formula

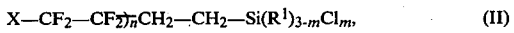   (II)

where $R^1$, X, m and n each have the same meaning as defined above, and an aliphatic carboxylic acid represented by the general formula

   (III)

where $R^2$ has the same meaning as defined above, in the presence of an acceptor for hydrogen chloride such as pyridine, triethylamine and the like.

The monovalent hydrocarbon group represented by the symbol $R^1$ has from 1 to 6 carbon atoms and exemplified by alkyl groups such as methyl, ethyl, propyl, butyl and hexyl groups and aryl groups such as phenyl group, among which lower alkyl groups, e.g. methyl, ethyl and propyl groups are preferred.

The monovalent hydrocarbon group represented by the symbol $R^2$ has from 7 to 21 carbon atoms and is preferably an aliphatic group, i.e. an alkyl group or an alkenyl group. Several of the examples of the groups suitable as $R^2$ are n-heptyl, n-nonyl, 2-ethylhexyl, undecyl, tridecyl, heptadecyl and heneicosyl groups as well as aliphatically unsaturated groups such as $C_{17}H_{33}-$ and $C_{17}H_{31}-$.

The symbol X at the terminal of the fluoroalkyl group represents a hydrogen atom or a fluorine atom, preferably, a fluorine atom. A hydrogen atom is less preferred as the atom X because of the poorer effectiveness of the compounds with a hydrogen atom as X than the compounds with a fluorine atom as X in improving the surface properties of articles of synthetic resins as well as the smaller availability of those compounds.

The number n in the general formula (I) is a positive integer not exceeding 4 although it may be larger than 4 if a starting chlorosilane compound of the general formula (II) having n larger than 4 is available. On the other hand, the number m in the general formula (I) is limited to 1, 2 or 3 and the compounds with m equal to 1 are less preferred because of the expensiveness of the starting chlorosilane compounds of the general formula (II) with m equal to 1 along with smaller effectiveness of the silane compounds of the general formula (I) derived therefrom.

Numbers of the fluoroalkyl-containing silane compounds in conformity with the general formula (I) and the definitions of the symbols above given have been synthesized by the inventors as listed in Table 1 hereunder.

Improvements of the surface properties of synthetic resin shaped articles can be achieved by merely coating the surface of the article with a very small amount of the silane compound of the general formula (I). When a lasting effect is desired with the silane compound, however, it is better to admix the synthetic resin with the silane compound together with other additive ingredients conventionally used in the fabrication of synthetic resins before the resin composition is shaped into articles. The amount of addition of the silane compound is determined depending on several factors such as the kind of the synthetic resin, desired nature of the surface to be improved, compatibility of the silane compound with the resin and the like. Generally speaking, the amount of the silane compound is in the range from 0.01 to 20 parts by weight or, preferably, from 0.05 to 10 parts by weight per 100 parts by weight of the synthetic resin. This is because smaller amounts than above cannot give sufficient effects of improving the surface properties while larger amounts of the silane compound than the above range do not give an additional advantages sometimes, instead, with drawbacks such as bleeding or blooming of the silane compound on the surface of the article and decrease of the mechanical strengths of the shaped articles.

When temporary improvements of the surface properties are desired, sufficient effects can be obtained by merely applying the silane compound on to the surface of the shaped article. When the silane compound is liquid at room temperature, the silane compound may be applied as such. It is recommendable that the silane compound is diluted with a suitable organic solvent, especially, when the silane compound is solid at room temperature or an excessive coating amount over necessity should be avoided by the reason of economy. Suitable organic solvents are exemplified by alcohols such as ethyl alcohol, propyl alcohol and butyl alcohol, glycols and derivatives thereof such as ethyleneglycol monomethyl ether, ethyleneglycol monoethyl ether and carbitol, aromatic hydrocarbons such as benzene, toluene and xylene, ketones such as methyl ethylketone and methylisobutylketone, esters such as ethyl acetate and butyl acetate and the like. These organic solvents can be used as a mixture of two kinds or more according to need.

The improving effect of the surface properties of synthetic resin obtained with the above described fluoroalkyl-containing organosilanes is so large that the synthetic resins as the objective material of the present invention are not limitative but the inventive method is applicable to almost all kinds of synthetic resins. Several of the typical examples of the resins suitable for the application of the inventive method are polyethylene resins, polypropylene resins, polyvinyl chloride resins, polystyrene resins, ABS resins, AS resins, SB resins, copolymeric resins of vinyl chloride and vinyl acetate, polymethyl methacrylate resins, saturated polyester resins, polyamide resins, polyurethane resins, epoxy resins, phenolic resins, amino resins, polycarbonate resins, polyfluoroolefin resins, cellulosic resins, silicone resins, polybutadiene resins, alkyd resins, melamine resins and the like.

When an article of a synthetic resins is shaped with admixture of the inventive fluoroalkyl-containing silane compound or the silane compound is applied on to the surface of the article, advantages are obtained that the surface lubricity of the article is increased with a decreased coefficient of surface friction leading to lesser susceptibility of the article to scratches and improved mold releasability. Most significantly, the effect of the fluoroalkyl-containing silane compound of the invention is not limited to shaped articles of synthetic resins but properties of coating compositions, e.g. paints and varnishes, of which the vehicle resin is one or a mixture of the above named synthetic resins, can be improved by the addition of the silane compound.

It is further noted that, in the fabrication of films and other shaped articles with a synthetic resin, the workability is remarkably improved by the addition of the inventive silane compound to the resin before fabrication.

Following are the examples to illustrate the synthetic preparation and properties of the inventive fluoroalkyl-containing silane compounds as well as the effects obtained by the addition of the silane compound to a synthetic resin or a coating composition.

EXAMPLE 1

Into a reaction vessel were introduced 565 g of oleic acid and 1000 g of toluene and the mixture was heated to 80° C. While the mixture was kept at this temperature, 561 g of a fluoroalkyl-containing chlorosilane expressed by the formula

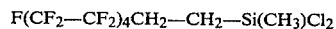

$F(CF_2-CF_2)_4CH_2-CH_2-Si(CH_3)Cl_2$ were added dropwise into the reaction mixture under agitation followed by further temperature elevation and the dehydrochlorination reaction was effected for 5 hours under reflux of toluene.

After completion of the reaction and cooling, 101 g of triethylamine were added to the reaction mixture to neutralize the hydrogen chloride and the precipitated hydrochloride of the amine was removed by filtration. The filtrate was subjected to distillation under reduced pressure to remove toluene, the excess amount of triethylamine and other low boiling materials. The remaining product weighing 978 g was a yellowish brown liquid at room temperature and identified to be a silane compound expressed by the formula

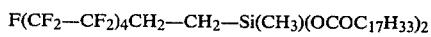

$F(CF_2-CF_2)_4CH_2-CH_2-Si(CH_3)(OCOC_{17}H_{33})_2$ by the infrared absorption spectral analysis, NMR spectral analysis and mass spectrometry.

Various kinds of fluoroalkyl-containing acyloxysilanes in conformity with the general formula (I) were synthesized each in a similar procedure to the above. The chemical formulas, melting points, densities at 25° C. or 90° C., viscosities at 25° C. and refractive indices at 25° C. of the thus synthesized silane compounds are summarized in Table 1 to follow.

EXAMPLE 2

A 1:1 by weight mixture of an epoxy resin (Epikote 1004, a product by Shell Chemical Co.) and linseed oil was heated to react the components and the reaction product was diluted with toluene to give a concentration of 50% by weight. A coating composition was prepared by blending 1 part by weight of the above obtained solution and 3 parts by weight of an acrylic resin (Aron 1001, a product by Toa Chemical Co.) with further addition of toluene to give a solid content of 40% by weight.

The thus obtained coating composition was admixed with 0.1% by weight of either one of the additive compounds indicated in Table 2 below including the Silanes No.4, No.5, No.8 and No.12 prepared in Example 1 and each of the coating compositions was applied on to the surface of two aluminum plates of 5 cm×10 cm wide by flow coating followed by air drying for 1 hour and baking at 105° C. for 20 minutes.

The test panels thus prepared were visually examined for the appearance of the coated surface and subjected to the tests for the coefficient of friction, sliding angle and scratch of the coated surfaces to give the results set out in Table 2. The tests for the sliding angle and scratch of the coated surface were undertaken as described below.

Sliding angle: two test panels were overlaid one on the other to have their coated surfaces in contact with each other in 5 cm×5 cm portions and a weight of 250 g was placed on the overlapping portion and the test panels were tilted gradually to find the angle at which the overlying test panel began to slide down on the underlying test panel.

paint, with which a test panel of aluminum was coated followed by curing of the paint by standing for 7 days at room temperature.

The thus coated test panels were examined for the appearance of the coated surfaces and the coefficients of friction and the sliding angles were determined in the same manner as in the preceding example to give the results set out in Table 3 below.

TABLE 1

| Silane No. | Organosilane compound | Melting point, °C. | Density, g/cm$^3$ (temperature) | Viscosity at 25° C. cS | Refractive index at 25° C. |
|---|---|---|---|---|---|
| 1 | $F(CF_2CF_2)_4CH_2CH_2Si(CH_3)(OCOC_{17}H_{33})_2$ | 7 | 1.14 (25° C.) | 50.2 | 1.420 |
| 2 | $F(CF_2CF_2)_4CH_2CH_2Si(CH_3)(OCOC_7H_{15})_2$ | 0 | 1.28 (25° C.) | 21 | 1.383 |
| 3 | $F(CF_2CF_2)_4CH_2CH_2Si(CH_3)(OCOC_{13}H_{27})_2$ | 48 | 1.02 (90° C.) | — | — |
| 4 | $F(CF_2CF_2)_4CH_2CH_2Si(OCOC_{21}H_{43})_3$ | 72 | 1.04 (90° C.) | — | — |
| 5 | $F(CF_2CF_2)_3CH_2CH_2Si(CH_3)(OCOC_7H_{15})_2$ | −1 | 1.19 (25° C.) | 23 | 1.394 |
| 6 | $F(CF_2CF_2)_3CH_2CH_2Si(OCOC_{17}H_{31})_3$ | −11 | 1.04 (25° C.) | 26 | 1.439 |
| 7 | $F(CF_2CF_2)_2CH_2CH_2Si(C_3H_7)(OCOC_7H_{13})_2$ | 0 | 1.10 (25° C.) | 21 | 1.398 |
| 8 | $F(CF_2CF_2)_2CH_2CH_2Si(CH_3)(OCOC_9H_{19})_2$ | 30 | 1.03 (90° C.) | — | — |
| 9 | $F(CF_2CF_2)_2CH_2CH_2Si(OCOC_{13}H_{27})_3$ | 47 | 1.00 (90° C.) | — | — |
| 10 | $F(CF_2CF_2)_2CH_2CH_2Si(CH_3)(OCOC_{17}H_{33})_2$ | 8 | 1.05 (25° C.) | 29 | 1.435 |
| 11 | $CF_3CF_2CH_2CH_2Si(CH_3)(OCOC_7H_{15})_2$ | −2 | 1.05 (25° C.) | 20 | 1.432 |
| 12 | $CF_3CF_2CH_2CH_2Si(OCOC_{17}H_{35})_3$ | 67 | 0.95 (90° C.) | — | — |
| 13 | $H(CF_2CF_2)_2CH_2CH_2Si(CH_3)(OCOC_7H_{15})_2$ | 0 | 1.11 (25° C.) | 18 | 1.398 |

Scratch of the coated surface: two test panels were overlaid one on the other and a weight of 250 g was placed on the overlapping portion of the test panels just in the same manner as in the test of the sliding angle. The overlying test panel was then removed forcibly by pulling and the thus rubbed surfaces of the test panels were examined visually to find the surface condition evaluated by the following criteria.

TABLE 2

| Additive | Coefficient of friction | Sliding angle | Scratch of coated surface | Appearance of coated surface |
|---|---|---|---|---|
| None | 0.87 | 37° | C | slight orange-peel |
| Dimethylsilicone fluid, 20 cS at 25° C. | 0.38 | 27 | B | good |
| Dimethylsilicon fluid, 500 cS at 25° C. | 0.91 | 47° | C | uneven spreading |
| Oleic acid | 0.69 | 36° | C | good |
| Caprylic acid | 0.67 | 35° | C | good |
| Silane No. 4 | 0.27 | 21° | A | good |
| Silane No. 5 | 0.24 | 18° | A | good |
| Silane No. 8 | 0.25 | 20° | A | good |
| Silane No. 12 | 0.25 | 18° | A | good |

A: no scratches and cloudiness
B: a few scratches and slight cloudiness
C: considerable scratches and cloudiness

EXAMPLE 3

A white enamel paint was prepared by blending 38 parts by weight of an alkyd resin (Beckosole ER-3400, a product by Nippon Reichhold Co.), 20 parts by weight of a butylated melamine resin (Super Beckamine G-821, a product by Nippon Reichhold Co.), 30 parts by weight of titanium dioxide and 12 parts by weight of xylene.

Either one of the additive ingredients indicated in Table 3 was added in an amount of 0.2 part by weight to 100 parts by weight of the above prepared white enamel

TABLE 3

| Additive | Coefficient of friction | Sliding angle | Appearance of coated surface |
|---|---|---|---|
| None | 0.58 | 32° | orange-peel |
| Dimethylsilicone fluid, 20 cS at 25° C. | 0.28 | 12° | good |
| Dimethylsilicone fluid, 500 cS at 25° C. | 0.47 | 25° | uneven spreading |
| Oleic acid | 0.49 | 28° | good |
| Caprylic acid | 0.55 | 31° | orange-peel |
| Silane No. 4 | 0.16 | 9° | good |
| Silane No. 5 | 0.15 | 9° | good |
| Silane No. 8 | 0.16 | 8° | good |
| Silane No. 12 | 0.18 | 12° | good |

EXAMPLE 4

A clear varnish was prepared by blending 100 parts by weight of an acrylic resin (Acrydic A-801, a product by Nippon Reichhold Co.), 15 parts by weight of a urethane resin (Vernoc D-750, a product by Nippon Reichhold Co.), 4 parts by weight of xylene and 1.5 parts by weight of either one of the additive ingredients indicated in Table 4 below and a plywood board was coated with it by use of a roller coater in a coating amount of 30 g/m$^2$ as dried followed by heating at 60° C. for 15 minutes to cure the varnish.

The coated surface was examined for the peeling resistance with an adhesive tape and destruction of the coating layer with an adhesive tape by the procedures described below as well as the scratch of the coated surface by the same procedure as in Example 2 to give the results set out in Table 4.

Peeling resistance: a cellophane-based pressure-sensitive adhesive tape of 1.8 cm width was bonded to the coated surface under a pressure of 1 kg/cm$^2$ and the resistance by peeling in g/cm was determined by use of a peeling tester.

Destruction of coating layer: the same adhesive tape was bonded in the same manner as in the above on to the coated surface and kept as such for 7 days at room temperature. Thereafter, the adhesive tape was rapidly peeled off the coated surface and the condition of the coated surface after peeling of the tape was examined visually.

TABLE 4

| Additive | Peeling resistance, g/cm | Destruction of coating layer | Scratch of coated surface |
|---|---|---|---|
| None | 180 | yes | C |
| Dimethylsilicone fluid, 350 cS at 25° C. | 160 | yes | B |
| Oleic acid | 180 | yes | C |
| Caprylic acid | 180 | yes | C |
| Silane No. 2 | 70 | no | A |
| Silane No. 6 | 65 | no | A |
| Silane No. 7 | 75 | no | A |
| Silane No. 10 | 60 | no | A |
| Silane No. 11 | 70 | no | A |

EXAMPLE 5

A resin composition was prepared by blending 100 parts by weight of a polyvinyl chloride resin (TK-1000, a product by Shin-Etsu Chemical Co.), 2.0 parts of calcium stearate, 3 parts by weight of calcium carbonate, 1 part by weight of a polyethylene wax, 0.5 part by weight of an auxiliary stabilizing agent and 0.2 part by weight of either one of the additive ingredients indicated in Table 5 below at 130° C. by use of a Henschel mixer. This resin composition was extruded into pellets with a single-screw extruder machine and the pellets were further extruded into rods of square cross section with the single-screw extruder machine.

TABLE 5

| Additive | Extrusion of pellets | | | Extrusion of square rods | | | Tensile properties | | | | Heat stability, minutes |
|---|---|---|---|---|---|---|---|---|---|---|---|
| | Torque, kg-cm | Pressure, kg/cm$^2$ | Rate of extrusion, g/min. | Torque, kg-cm | Pressure, kg/cm$^2$ | Rate of extrusion, g/min. | Yield point, kg/mm$^2$ | Tensile strength kg/mm$^2$ | Elongation, % | Impact strength, kg . cm/cm$^2$ | |
| None | 4.3 | 405 | 45.5 | 4.6 | 280 | 35.0 | 5.36 | 5.59 | 160 | 10.8 | 130 |
| Lead soap | 3.6 | 380 | 50.8 | 4.5 | 235 | 36.8 | 5.37 | 5.84 | 158 | 9.9 | 95 |
| Silane No. 1 | 4.3 | 400 | 54.5 | 4.6 | 245 | 35.8 | 5.40 | 5.70 | 170 | 12.4 | 135 |
| Silane No. 3 | 4.0 | 360 | 53.9 | 4.1 | 200 | 35.9 | 5.36 | 5.68 | 175 | 14.8 | 150 |
| Silane No. 6 | 3.2 | 295 | 51.6 | 3.1 | 170 | 31.2 | 5.35 | 5.63 | 170 | 13.1 | 135 |
| Silane No. 9 | 3.8 | 360 | 59.9 | 4.5 | 200 | 37.5 | 5.42 | 5.82 | 165 | 14.6 | 150 |

The values of torque in kg-cm, pressure in kg/cm$^2$ and rate of extrusion in g/mixture in the extruder machine were recorded during the extrusion of the above pellets and the square rods and the square rods were examined for the tensile properties, i.e. yielding point in kg/mm$^2$, tensile strength in kg/mm$^2$ and ultimate elongation in % and impact strength in kg.cm/cm$^2$ as well as the heat stability in minutes to give the results set out in Table 5. The measurements of the tensile properties and the impact strength were carried out at 20° C. in accordance with the procedure specified in JIS K 6745 and the heat stability was determined by recording the time in minutes to blackening of the sample kept at 180° C. in a Geer's oven.

As is clear from the results shown in Table 5, the inventive silane compounds are very effective in improving the workability of the resin compositions formulated therewith and also in improving the properties of the shaped articles formed with the resin composition even in comparison with the resin composition formulated with the lead soap which has been considered to be the best if setting aside the problem of toxicity as the reason of the abolished use of the lead formulations.

What is claimed is:

1. A fluoroalkyl-containing acyloxy silane represented by the general formula $$X\text{-}(CF_2\text{-}CF_2)_n CH_2\text{-}CH_2\text{-}Si(OCOR^2)_m(R^1)_{3-m},$$

in which $R^1$ is a monovalent hydrocarbon group having from 1 to 6 carbon atoms, $R^2$ is a monovalent hydrocarbon group having from 7 to 21 carbon atoms, X is a hydrogen atom or a fluorine atom, n is a positive integer not exceeding 4 and m is a positive integer not exceeding 3.

2. The fluoroalkyl-containing acyloxy silane as claimed in claim 1 wherein the monovalent hydrocarbon group represented by the symbol $R^1$ is selected from the class consisting of methyl, ethyl and propyl groups.

3. The fluoroalkyl-containing acyloxy silane as claimed in claim 1 wherein the monovalent hydrocarbon group represented by the symbol $R^2$ is selected from the class consisting of alkyl groups and alkenyl groups having from 7 to 21 carbon atoms.

4. The fluoroalkyl-containing acyloxy silane as claimed in claim 1 wherein X is the general formula is a fluorine atom.

5. The fluoroalkyl-containing acyloxy silane as claimed in claim 1 wherein the positive integer represented by the symbol m is 2 or 3.

* * * * *